United States Patent
Gann

(10) Patent No.: US 7,183,532 B2
(45) Date of Patent: Feb. 27, 2007

(54) DETECTING A DEFECT IN AN IMAGE SCANNER

(75) Inventor: Robert G. Gann, Bellvue, CO (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 930 days.

(21) Appl. No.: 09/845,852

(22) Filed: Apr. 30, 2001

(65) Prior Publication Data
US 2002/0158192 A1 Oct. 31, 2002

(51) Int. Cl.
*G01J 1/44* (2006.01)
*H04N 9/64* (2006.01)
*G06K 15/00* (2006.01)

(52) U.S. Cl. .................. 250/214 C; 348/246; 382/274; 358/3.26

(58) Field of Classification Search ................. 250/234, 250/226, 559.01, 559.4–559.46, 339.11, 341.7, 250/341.8, 330; 356/237.1, 237.4, 238.1, 356/239.1; 358/471, 406, 445, 463, 487, 358/484, 475; 348/251, 96–97; 382/275, 382/191, 318
See application file for complete search history.

(56) References Cited

U.S. PATENT DOCUMENTS

| | | | |
|---|---|---|---|
| 4,680,638 A * | 7/1987 | Childs .......................... 348/97 |
| 5,266,805 A | 11/1993 | Edgar .......................... 250/330 |
| 5,285,293 A | 2/1994 | Webb et al. ................. 358/471 |
| 5,526,040 A * | 6/1996 | Foley ........................... 348/97 |
| 5,589,887 A | 12/1996 | Wischermann |
| 5,801,962 A | 9/1998 | Sheu et al. |
| 5,969,372 A | 10/1999 | Stavely et al. .......... 250/559.42 |
| 6,026,174 A * | 2/2000 | Palcic et al. ................ 382/133 |
| 6,035,072 A | 3/2000 | Read |
| 6,075,590 A | 6/2000 | Edgar ........................ 356/237.1 |
| 6,518,587 B2 * | 2/2003 | Rombola .................. 250/559.1 |
| 6,683,643 B1 * | 1/2004 | Takayama et al. .......... 348/247 |
| 2002/0122213 A1 * | 9/2002 | Hill et al. .................... 358/484 |

FOREIGN PATENT DOCUMENTS

| | | |
|---|---|---|
| GB | 2140245 | 11/1984 |
| JP | 2000050023 | 2/2000 |
| WO | WO98/31142 | 7/1998 |

OTHER PUBLICATIONS

U.S. Appl. No. 09/629,495; "Dust And Scratch Detection For An Image Scanner"; Robert G. Gann et al.

* cited by examiner

*Primary Examiner*—Thanh X. Luu
(74) *Attorney, Agent, or Firm*—Augustus W. Winfield

(57) ABSTRACT

Image data in an image scanner is examined to determine whether lines (light or dark) are present in the image data. By examining whether the lines are present in image data for multiple colors, and whether calibration gains for corresponding photosensors are normal, it can be determined whether the lines are likely caused by a surface defect, on a calibration target, or on a platen, or on an image being scanned.

7 Claims, 5 Drawing Sheets

DETECTING A DEFECT IN AN IMAGE SCANNER

FIELD OF INVENTION

This invention relates generally to devices for digital electronic scanning of images and more specifically to detection of dust and scratches and other surface defects.

BACKGROUND OF THE INVENTION

Electronic image scanners convert an optical image into an electronic form suitable for storage, transmission or printing. In a typical image scanner, light from an image is focused onto line-arrays of photosensors for scanning one line at a time. A two dimensional image is scanned by providing relative movement between the photosensor line-arrays and the original image. In general, a color scanner measures the intensity of at least three relatively narrow bands of wavelengths of visible light, for example, bands of red, green and blue.

For image scanners, the digitized image may be degraded by the presence of artifacts on the surface of the object being scanned, such as dust and fingerprints, or defects in the surface of the object being scanned, such as scratches, folds, or textured surfaces. Multiple methods have been disclosed for detecting defects on transparent media. See, for example, U.S. Pat. No. 5,266,805, U.S. Pat. No. 5,969,372, and EP 0 950 316 A1. Some of the methods in the referenced patent documents utilize the fact that the dyes in transparent color film are essentially transparent to infrared light, whereas dust and scratches are relatively opaque. Other disclosed methods utilize dark field imaging, in which the light reaching the photosensors is reflected or diffracted by defects instead of the film.

Scanners for opaque media are configured differently than scanners for transmissive media, and different detection methods are needed. Commonly assigned U.S. patent application Ser. No. 09/629,495, filed Jul. 3, 2000 discloses defect detection, in an opaque media scanner, having multiple spaced-apart line-arrays of photosensors, where surface defects cast shadows, and the length of the shadows, as seen by each line-array of photosensors, varies among the different line-arrays of photosensors.

Reflective document scanners and copiers commonly provide a fixed-position calibration target, along a scanline dimension. In a flat bed scanner with a motionless document being scanned, the calibration target is typically beneath a glass platen in a relatively dust free environment. The calibration target is used to compensate, before scanning, for variation in sensitivity of individual photosensors, and for variation in light intensity along the length of the scanline. The process is called Photo-Response Non-Uniformity (PRNU) calibration. See, for example, U.S. Pat. No. 5,285,293. Since the calibration target is presumably uniform, any pixel to pixel intensity variation can be attributed to sensor sensitivity, light source variation, or other system uniformity. A correction factor (gain and/or offset) is calculated and applied to subsequent scans. Just in case there is a surface defect on the calibration target, it is known in commercially available scanners to accumulate data from many scanlines (the photosensors are moved relative to the calibration target) during PRNU calibration, and to average the data on a photosensor-by-photosensor basis. It is also known to discard extreme data points before averaging. For example, given ten intensity measurements for one photosensor, it is known to discard the lowest and highest intensity values, and then average the remaining eight values. This helps eliminate the effects of surface defects on the calibration target during PRNU calibration.

Of particular concern in the present application is scanners in which a document moves past a stationary photosensor array, for example, scroll-feed scanners, and flat-bed scanners with automatic document feeders. Scroll-feed scanners and scanners with automatic document feeders have several unique problems regarding detection and correction of surface defects. In a scroll-feed scanner, the document may be displaced from a platen, so the calibration target is typically behind the document being scanned to properly measure the light at the document. This in turn causes three potential problems. First, the calibration target is much more susceptible to debris introduced by documents, particularly paper debris. Second, the photosensor array is typically stationary, so the technique of averaging multiple scanlines to eliminate the effects of surface defects during PRNU calibration is not applicable. Third, if the calibration target is behind the document being scanned, and if there is debris on the calibration target, then the PRNU calibration compensates for the debris, but subsequent document scanning hides the debris on the calibration target so that the PRNU gain or offset is inappropriate. The result is a streak in the digitized image. Finally, with moving documents, it is common for debris to become temporarily trapped between the document and a glass platen, and then later the debris may be dislodged. Again, the result is a streak in the digitized image.

There is a need for surface defect detection for the unique situations presented by moving documents: (1) debris on the calibration target with a stationary photosensor array, and (2) temporary debris on a platen during scanning.

SUMMARY OF THE INVENTION

Narrow streaks (light or dark), corresponding to a few photosensors, appearing primarily in one color channel, are analyzed to see if the streaks are likely caused by a surface defect, either on the calibration target or on the platen. Debris on the calibration target causes the PRNU gain for some photosensors to be abnormally high. If the debris is later hidden by the document being scanned, the result is a high intensity streak for one color channel in the digitized image. Accordingly, images are searched for a high intensity streak in one color channel of the digitized image corresponding to an anomalous PRNU gain. Debris on the platen introduced after PRNU calibration results in a low intensity streak in one color channel, with normal corresponding PRNU gains. Accordingly, the system may also search for a low intensity streak in one color channel of the digitized image with a normal corresponding PRNU gain. For scanners with multiple line-arrays of the same or nearly the same color, detection is simplified. With two line-arrays of nearly the same color, if a light or dark streak appears in data from only one of the light arrays, it is likely caused by a defect. Examining the corresponding PRNU gains may aid in determining the cause of the defect.

DETAILED DESCRIPTION OF THE PREFERRED EMBODIMENT OF THE INVENTION

Figure 1:
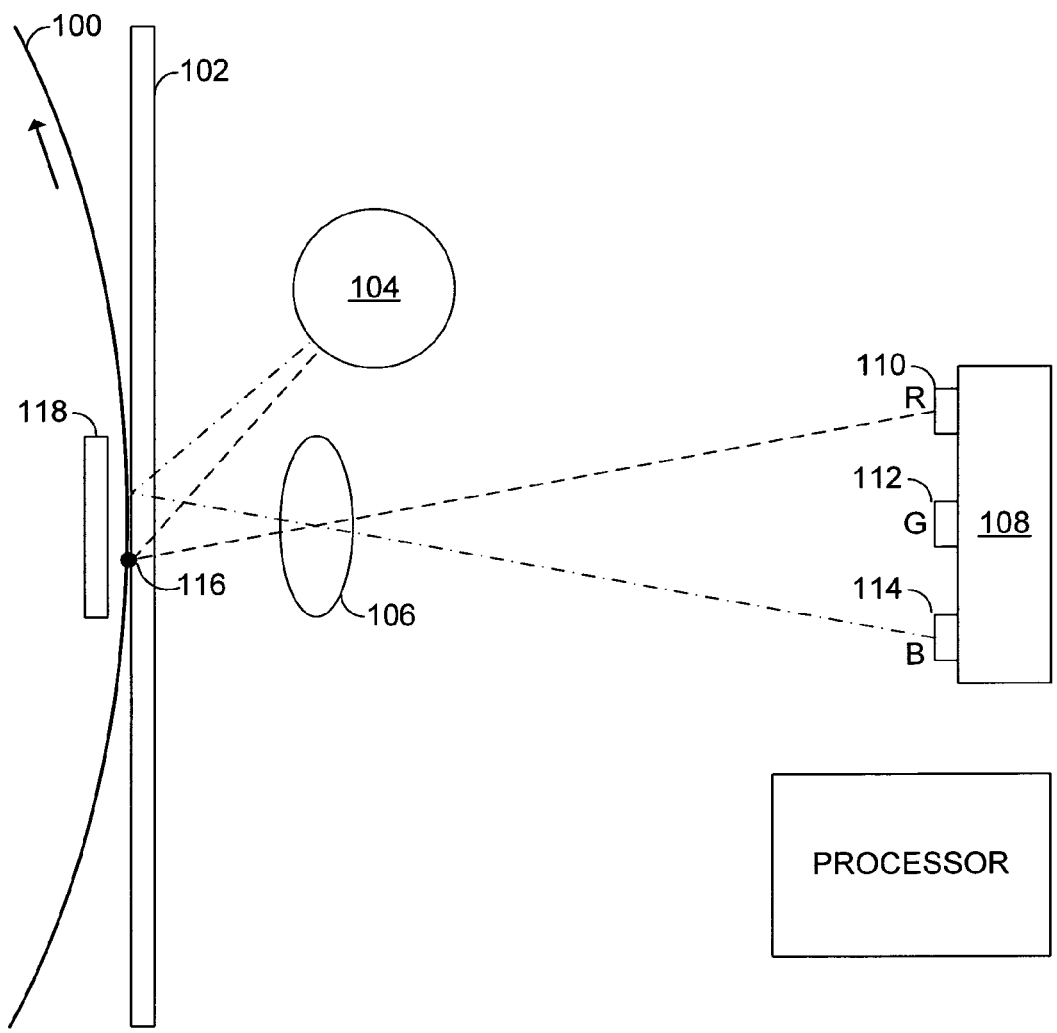
FIG. 1 is a block diagram side view of a scanner with a moving document.

In FIG. 1, a document 100 is being moved adjacent to a transparent platen 102. The direction of movement is indicated by an arrow. The document is illuminated by a lamp 104. An objective lens 106 focuses light, scattered from scanlines on the surface of the document 100, onto line-arrays of photosensors. A photosensor assembly 108 has three line-arrays of photosensors (110, 112, 114), designated R, G, and B for red, green, and blue. FIG. 1 illustrates a scanner with an objective lens, but the invention is equally applicable to contact imaging photosensor arrays, fibre-optic imaging, and photosensor arrays using rod lens arrays.

Light scattered by a first scanline on the document 100 is focused, by the lens 106, onto the red line-array 110. Light scattered by a second scan-line is focused onto the blue line-array 114. A dust particle 116 (exaggerated to facilitate illustration) lies on the scanline for the red line-array 110.

A calibration target 118 is located behind the document 100 (as seen by the photosensor assembly 108). Before the document 100 is inserted, the lamp 104 illuminates the calibration target, and PRNU calibration is performed. Dust particle 116 may alternatively be located on the calibration target 118 along the line that is focussed onto the red line-array 110.

Signals from the line-arrays of photosensors (110, 112, 114) are typically amplified by at least one amplifier (not illustrated), converted to digital values by at least one analog-to-digital converter (not illustrated), and the resulting digital values are stored in a memory (not illustrated) where they may be analyzed by a processor (not illustrated). PRNU calibration determines a gain used by the system for the signal from each photosensor, where that gain may be an analog amplifier gain, or the gain may be a digital gain that is part of a computation on the digital values. That is, the signal from each photosensor has an associated unique gain determined by PRNU calibration. The signal processing and data processing for one line-array is commonly referred to as a color channel.

First, consider the situation in which the dust particle 116 is on the surface of the calibration target 118, and where document 100 is not present. At least one photosensor in line-array 110 receives a low intensity, and the PRNU calibration increases the gain used for the affected photosensors. Then, when the document 100 is scanned, the PRNU gain for at least one photosensor in line-array 110 is excessively high, resulting in intensity measurements that indicate an intensity much higher than the actual intensity. The result is a high intensity line or streak in the red image data (before any color transformation is computed), along the direction of movement of the document. Assuming that the dust particle 116 does not affect scanlines for other line-arrays, there is no corresponding streak in the blue or green image data.

The PRNU calibration data is searched to see if the PRNU gains for any individual photosensors exceed a predetermined threshold. For the example of FIG. 1, the red image data, before any color transformation is computed, corresponding to the photosensors with an abnormally high PRNU gain, are examined to determine whether there is an intensity, along the dimension of the image corresponding to movement of the document 100, that exceeds a predetermined threshold. If there is a photosensor with an abnormally high PRNU gain, and a corresponding high intensity line or streak in the image data, then it is likely that there was a surface defect on the calibration target during PRNU calibration. Note that a high intensity streak in the image data could be a legitimate part of the image. For example, a red line on the document being scanned would appear as a high intensity strip in the red digitized image data. However, by starting with high PRNU gain, and looking only at the data corresponding to high PRNU gain, the probability that the high intensity data represents a legitimate part of the image is greatly reduced.

There are multiple alternatives for compensation for the surface defect. The image data can be recomputed with a lower PRNU gain for photosensors that are identified as having an abnormally high PRNU gain. However, if some digital data values are clipped at a maximum value, then some information has been irretrievably lost. Alternatively, the PRNU gain can be corrected and the image can be rescanned. Alternatively, the digitized image may be edited to replace the pixels in the high intensity streak with a combination of the intensity values from nearby pixels. For example, a pixel can be replaced with the average value of adjacent pixels, or bilinear interpolation using four neighboring pixels can be used, or more general resampling techniques can be used. If the image data is modified, the operator can be alerted that the image is being modified, and the operator can accept or decline the modification. Preferably, the operator is presented with an image with the correction and an image without the correction, and the operator is permitted to choose between the two. The system can also request that the operator clean the calibration target. Finally, PRNU calibration can be performed again, and if the abnormally high gains have not changed, then the PRNU gain for the photosensors corresponding to the identified defect can be adjusted for subsequent scans.

Now consider the situation in which the dust particle 116 is introduced onto the platen 102 after PRNU calibration. The dust particle may be present for an entire scan of a document, or may appear and disappear during the scan of a document. The result is a line or streak of low intensity in the data for a single color channel (before any color transformation computation). For example, in FIG. 1, there would be a line of low intensity in the red data, but not in the blue or green data. The PRNU data for the red photosensors is examined to see if the PRNU gain, for the photosensors corresponding to the dark line, exceeds a predetermined threshold. If so, then it is likely that the dust particle was present on the platen during PRNU calibration. If the dust particle was present on the platen during PRNU calibration, and is still present, then the dust particle is blocking the light, for at least one photosensor, from the image being scanned, and PRNU gain adjustment is unlikely to help. In that case, the image may be edited to replace the pixels in the dark streak with a combination of the intensity values from nearby pixels. For example, a pixel can be replaced with the average value of adjacent pixels, or bilinear interpolation using four neighboring pixels can be used, or more general resampling techniques can be used. Again, the operator can be alerted and to the operator can decide whether to proceed with image modification.

Note that there are other potential causes of a low intensity streak. A black or dark line in the image being scanned would result in a low intensity streak in all color channels. A high intensity streak, in the image being scanned, of one color, may result in a low intensity streak in other colors. For example, if the filters were ideal, then a green line in the image being scanned would result in low intensity data in the red and blue color channels. However, real filters or color separators typically used for image scanning have some spectral overlap, so that a green line in the image being scanned might result in a relatively low intensity for the corresponding red and blue photosensors, but not as low as the intensity resulting from a black line or from an occluded photosensor. Again, thresholding can be used. If a dark streak in the red data has a corresponding relatively dark streak in only one of the green data and blue data, then the streak may be a legitimate part of the image.

If a dark streak appears only in one color channel, and the PRNU gains for the corresponding photosensors do not exceed the predetermined threshold, then it is likely that a dust particle appeared after the PRNU calibration Again, gain adjustment is unlikely to help, and the image may be edited to replace the pixels in the dark streak with a combination of the intensity values from nearby pixels.

Figure 2:
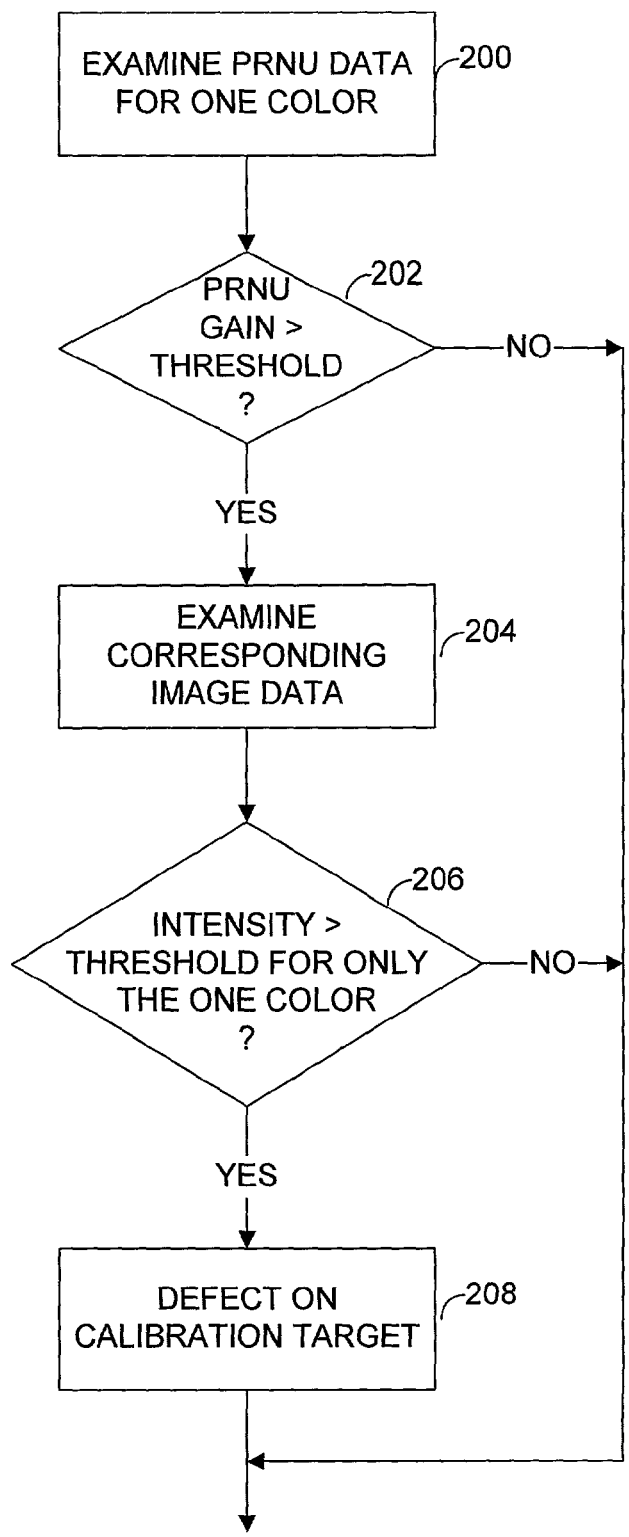
FIG. 2 is a flow chart of an example method for determining that a defect exists on a PRNU calibration target.

FIG. 2 illustrates an example method for determining that a defect appears on the calibration target. At step 200, the PRNU gain data for one color channel is examined. At decision 202, if the PRNU gain for any photosensors exceeds a predetermined threshold, then at step 204 the corresponding pixels in the image data (before color transformation) are examined. At decision 206, if the intensity data for the pixels corresponding to the high PRNU gain values also exceeds a predetermined threshold, then at step 208 the system determines that there is a defect on the PRNU calibration target. The process illustrated in FIG. 2 is repeated for each abnormally high PRNU gain, as necessary, and is repeated for all colors.

Figure 3:
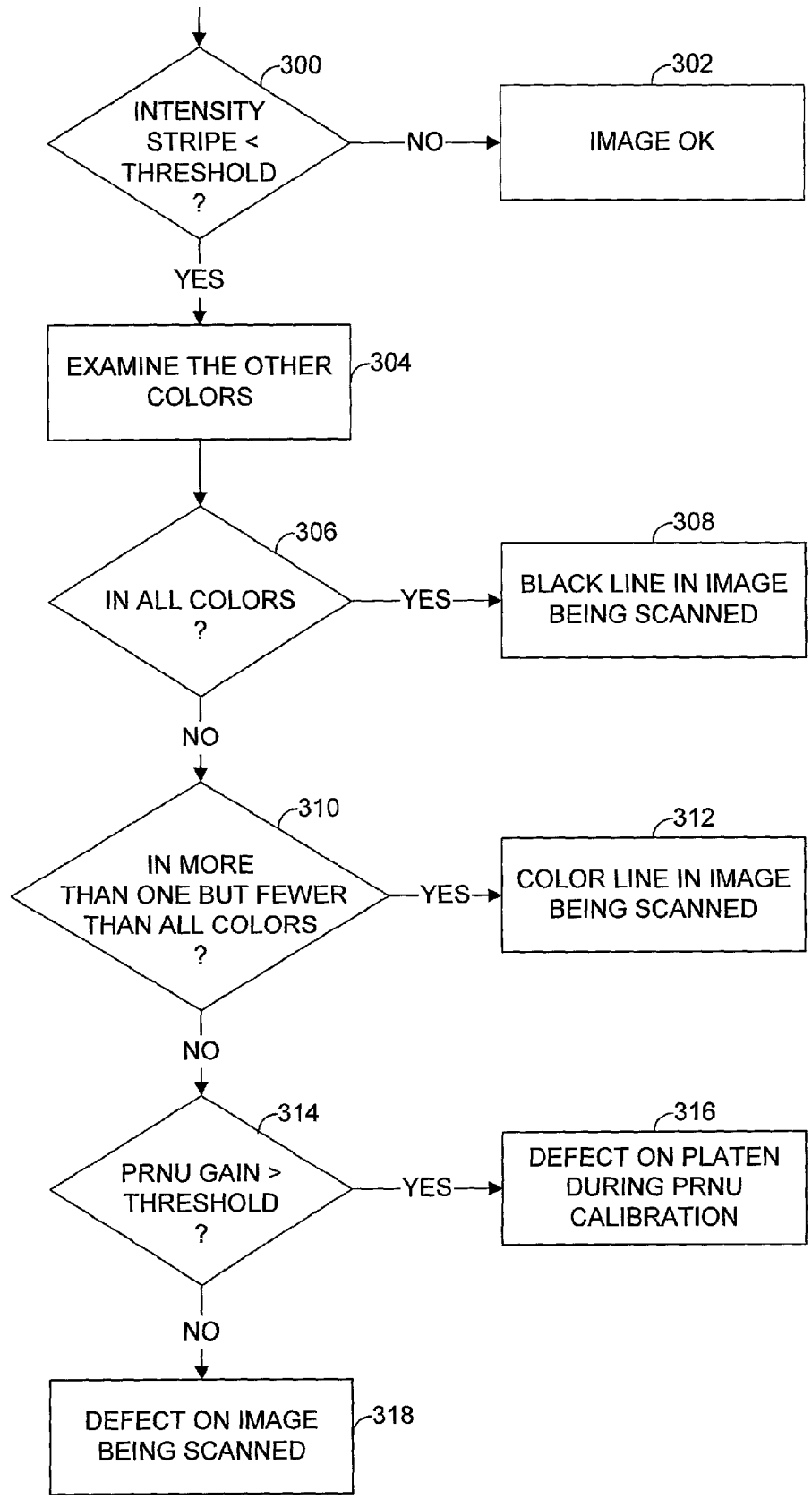
FIG. 3 is a flow chart of an example method for determining that a defect exists on a platen or on an image being scanned.

FIG. 3 illustrates an example method for determining that there is a defect on the platen that was present during PRNU calibration, or that there is a defect on the platen or on the image being scanned that was not present during PRNU calibration. Preliminary to step 300, the image data for one color channel (before color transformation) is examined to see if there is a stripe, in the direction of document movement, having a low intensity. That is, for multiple scanlines, the intensity of the Nth pixel in the scanlines is less than a predetermined threshold. At decision 300, if a low intensity stripe has been detected, then at step 304 the corresponding pixels in the image data for other color channels are examined. At decision 306, if there is a low intensity stripe for all colors, then at step 308 the system determines that there is a dark line in the image being scanned. At decision 310, if there is a low intensity stripe for more than one color, but not all colors, then at step 312 the system determines that there is a color line in the image being scanned. At decision 314, it has been determined that there is a low intensity stripe in the image data for only one color. If the PRNU gain data, for photosensors corresponding to the low intensity stripe, indicate an abnormally high PRNU gain, then at step 316 the system determines that there was a defect (for example, on the platen) present during PRNU calibration and the defect is still present. If the PRNU gain data, for photosensors corresponding to the low intensity stripe, indicate normal PRNU gains, then at step 318 the system determines that there is a defect on the platen or on the image being scanned. For either step 316 or step 318, the only effective compensation for the defect is image editing (gain adjustment will not help). For that reason, decision 314 is optional. Note also that the conclusion at step 316 cannot distinguish between a defect on the platen and a bad photosensor, but from a practical standpoint this may not matter. That is, in either case, image correction may be required.

A photosensor assembly may have multiple spaced-apart line-arrays that receive light having the same spectral bandwidth, or almost the same spectral bandwidth. For example, a photosensor assembly may have one set of line-arrays with relatively small photosensors having a relatively high sampling rate but relatively low signal-to-noise, and a separate set of line-arrays with relatively large photosensors having a relatively low sampling rate but relatively high signal-to-noise. Having two different sizes of photosensors provides substantial versatility in scanning. Given a photosensor assembly with multiple rows of the same color, defect detection is substantially simplified. With two line-arrays of nearly the same color, if a light or dark streak appears in data from only one of the line-arrays, it is likely caused by a defect.

Figure 4:
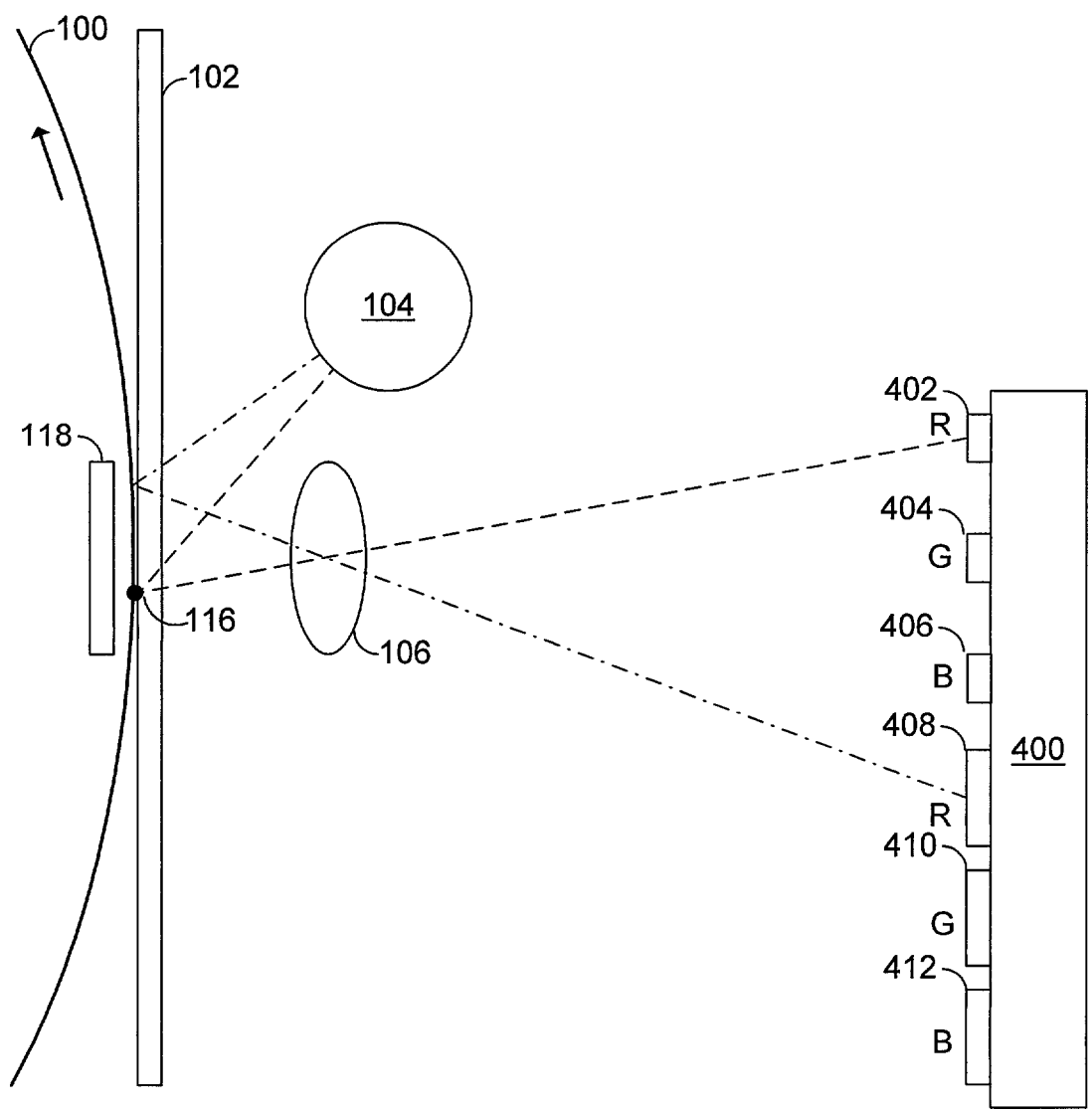
FIG. 4 is a block diagram side view of a scanner with a moving document with an alternative configuration for the photosensor assembly.

FIG. 4 illustrates an example scanner of the general type illustrated in FIG. 1, but with a photosensor assembly having multiple line-arrays of each color. In FIG. 4, photosensor assembly 400 has three line-arrays of relatively small photosensor (402, 204, 406), and three line-arrays of relatively large photosensors (408, 410, 412). As illustrated in FIG. 4, line-arrays 402 and 408 receive red light, line-arrays 404 and 410 receive green light, and line-arrays 406 and 412 receive blue light. Two line-arrays of the same "color" (for example, line arrays 402 and 408) may receive identical spectral bandwidths of light, or they may receive spectral bandwidths that substantially overlap but are slightly different. For purposes of the example embodiment of the invention, it does not matter whether the two sets of photosensors are of the same size, or different sizes, and it does not matter whether the spectral bandwidths are identical, or almost the same.

Figure 5:
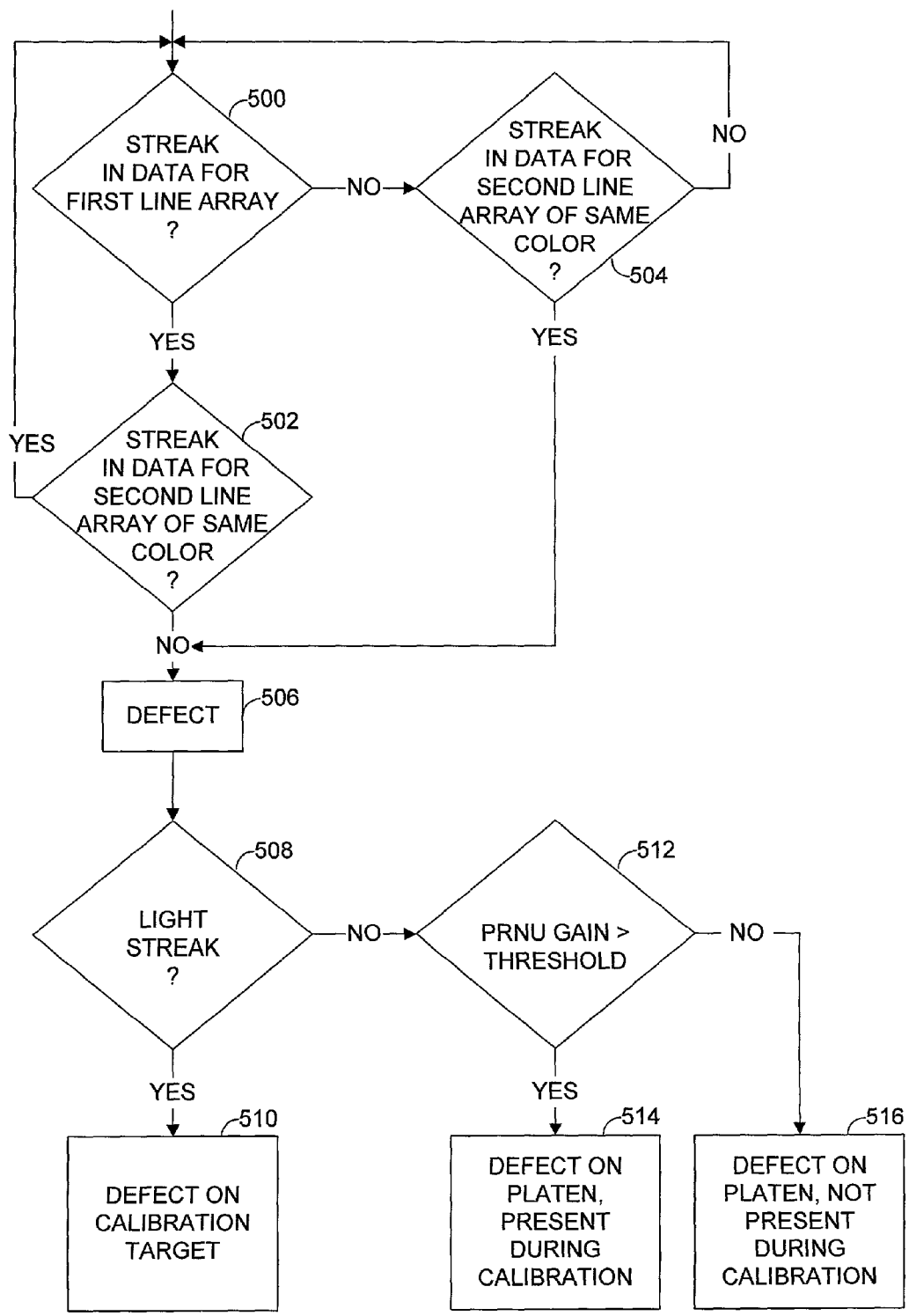
FIG. 5 is a flow chart of an example method for determining that a defect exists when using a photosensor assembly as in FIG. 4.

FIG. 5 illustrates an example flow chart for a method of detecting defects when the scanner has two line-arrays of nearly the same color. In decisions 500, 502, and 504, if a streak (light or dark) appears in the digitized intensity data for only one of two line-arrays receiving light having the same or almost the same spectral bandwidths, then at step 506 the streak indicates a defect. The rest of the steps illustrated in FIG. 5 are optional, and may be executed if additional diagnostic information is desired. At decision 508, if the streak is a light (high intensity) streak, then at step 510 there is likely a defect on the calibration target. At decision 512, if the streak is dark (low intensity) and if the corresponding PRNU gains are greater than a predetermined threshold, then at step 514 there is likely a defect on the platen that was present during PRNU calibration. At decision 512, if the streak is dark (low intensity) and if the corresponding PRNU gains are not greater than a predetermined threshold, then at step 516 there is likely a defect on the platen that was not present during PRNU calibration. Note that the conclusion at step 514 cannot distinguish between a defect on the platen and a bad photosensor, but from a practical standpoint this may not matter. That is, in either case, image correction may be required.

The foregoing description of the present invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method, in an image scanner, for detecting a defect, comprising:
    determining whether at least one line is present in image data for a particular color channel;
    determining whether a calibration gain for a photosensor corresponding to the line is normal; and
    generating an improved image when the calibration gain is not normal.

2. A method for detecting a defect on a calibration target for an image scanner, comprising:
    determining that a gain associated with a particular photosensor, in a particular line-array of photosensors, in a photosensor assembly, exceeds a predetermined gain threshold, the gain having been calibrated using the calibration target;
    determining that an image intensity measurement for the particular photosensor exceeds a predetermined intensity threshold;
    determining that an image intensity measurement for each photosensor, physically corresponding to the particular photosensor, in all line-arrays in the photosensor assembly other than the particular line-array of photosensors, does not exceed the predetermined intensity threshold; and
    generating an improved image.

3. A scanner, comprising:
    a first line-array of photosensors;
    a second line-array of photosensors;
    a processor; and
    the processor determining that a defect exists when lines are present in image data from only one of the first and second line-arrays of photosensors and when calibration gains, associated with photosensors corresponding to the lines, are normal.

4. A scanner, comprising:
    a calibration target;
    a photosensor assembly comprising a plurality of line-arrays of photosensors;
    a processor;
    a particular photosensor, in a particular line-array of photosensors, in the photosensor assembly, having an associated gain that exceeds a predetermined gain threshold, the gain having been calibrated using the calibration target;
    the particular photosensor having an associated image intensity measurement that exceeds a predetermined intensity threshold; and
    the processor determining that a defect exists when an image intensity measurement for each photosensor physically corresponding to the particular photosensor, in all line-arrays in the photosensor assembly other than the particular line-array of photosensors, does not exceed the predetermined intensity threshold.

5. A scanner, comprising:
    a calibration target;
    a photosensor assembly comprising a plurality of line-arrays of photosensors;
    a processor;
    a particular photosensor, in a particular line-array of photosensors, in a photosensor assembly, having an associated image intensity measurement that is less than a predetermined intensity threshold; and
    the processor determining that a defect exists when an intensity output, for each photosensor physically corresponding to the particular photosensor, in all line-arrays in the photosensor assembly other than the particular line-array of photosensors, is not less than the predetermined intensity threshold.

6. The scanner of claim 5, further comprising:
    the processor determining that the defect was present during calibration, by determining that a gain associated with the particular photosensor, determined during calibration, exceeds a predetermined gain threshold.

7. The scanner of claim 5, further comprising:
    the processor determining that the defect was not present during calibration, by determining that a gain associated with the particular photosensor, determined during calibration, does not exceed a predetermined gain threshold.

* * * * *

UNITED STATES PATENT AND TRADEMARK OFFICE
CERTIFICATE OF CORRECTION

| | | |
|---|---|---|
| PATENT NO. | : 7,183,532 B2 | Page 1 of 1 |
| APPLICATION NO. | : 09/845852 | |
| DATED | : February 27, 2007 | |
| INVENTOR(S) | : Robert G. Gann | |

It is certified that error appears in the above-identified patent and that said Letters Patent is hereby corrected as shown below:

On the title page, item (54), in column 1, in "Title", line 1, after "IMAGE" insert -- IN AN IMAGE --.

In column 1, in "Title", line 1, after "IMAGE" insert -- IN AN IMAGE --.

In column 1, line 39, delete "Jul. 3, 2000" and insert -- Jul. 31, 2000 --, therefor.

In column 4, line 64, after "and" delete "to".

Signed and Sealed this

Nineteenth Day of May, 2009

JOHN DOLL
*Acting Director of the United States Patent and Trademark Office*